United States Patent [19]

Buck

[11] 4,362,712

[45] Dec. 7, 1982

[54] CARBOXYLATED NAPHTHALENE FORMALDEHYDE CONDENSATION POLYMERS AS DENTAL PLAQUE BARRIERS

[75] Inventor: Carl J. Buck, Berkeley Heights, N.J.

[73] Assignee: Johnson & Johnson Products, Inc., New Brunswick, N.J.

[21] Appl. No.: 172,494

[22] Filed: Jul. 25, 1980

[51] Int. Cl.$^3$ .................... A61K 7/16; A61K 31/765; C08G 6/00; C08G 2/00
[52] U.S. Cl. ........................................ 424/49; 424/82; 424/315; 528/230
[58] Field of Search ............................ 424/49, 56, 78; 528/230

[56] References Cited

U.S. PATENT DOCUMENTS 4,138,477  2/1979  Gaffar .................................... 424/52
4,183,914  1/1980  Gaffar et al. ........................... 424/48
4,188,373  2/1980  Krezanoski ........................... 424/78

*Primary Examiner*—Douglas W. Robinson

[57] ABSTRACT

Polymers useful in compositions and methods for preventing the attachment of dental plaque to the surface of the teeth of mammals comprise alkali metal salts of certain carboxylated naphthalene formaldehyde polymers in a pharmaceutically acceptable vehicle and the periodic application thereof to teeth.

4 Claims, No Drawings

CARBOXYLATED NAPHTHALENE FORMALDEHYDE CONDENSATION POLYMERS AS DENTAL PLAQUE BARRIERS

TECHNICAL FIELD

This invention relates to certain carboxylated aromatic polymeric compounds, to oral hygiene compositions comprising these polymeric compounds, and to methods using such compositions to prevent attachment of bacteria to teeth. More particularly, it relates to certain carboxylated polymeric materials that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

The Invention

Certain hydrophilic carboxylic acid and carboxylic acid salt derivatives of certain naphthalene formaldehyde condensation polymers have been synthesized. The salts of these polymers inhibit the deposition of dental plaque onto human teeth. These hydrophilic polymeric carboxylates are substantially soluble in water or water/organic solvent vehicles, have good film forming characteristics and, accordingly, are applied to teeth from various dentifrice formulations, mouth rinses, or other oral hygiene procedures. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. The carboxylated polymers of this invention are especially effective as components of dentifrices and other oral hygiene preparations in reducing dental plaque deposition on teeth.

The hydrophilic, polymeric carboxylates found useful for dental plaque control in accordance with the present invention are essentially carboxylic acid salt derivatives of formaldehyde condensation polymers of certain naphthalene compounds wherein the repeating unit of the polymer has the structure (A),

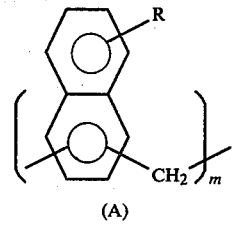

(A)

wherein R is selected from the group consisting of —COOM and —CH$_2$COOM (including mixtures of these two substituents), and M is selected from the group consisting of lithium, sodium and potassium. The free acids (wherein M is hydrogen), while too insoluble in aqueous media to be useful as barrier agents in the compositions of this invention, are new compositions of matter that are readily converted to the above salts by methods well known to those skilled in the art and are, therefore, considered to be within the scope of this invention as useful precursors of the salts used as barrier agents in the compositions and method of this invention.

The formaldehyde polymers of this invention are preferably prepared by the acid catalyzed condensation of aqueous 37% formaldehyde or paraformaldehyde with naphthoic acid and/or naphthylacetic acid under standard conditions reported in the literature for other compounds and reviewed extensively in the text by J. F. Walker, "Formaldehyde", R. E. Krieger Publishing Co., Third Edition, 1975. The resultant polymers, having repeating units of structure (A), wherein M is hydrogen, are converted to their alkali metal salts by neutralization or ion-exchange reactions.

Typical naphthalene compounds which can be utilized for preparation of the formaldehyde polymers of this invention are 1-naphthoic acid, 2-naphthoic acid, 1-naphthylacetic acid, and 2-naphthylacetic acid. The exact position for orientation of the methylene (—CH$_2$—) linkages on the aromatic rings is not known and is generally recognized as being complex and varied. It is well understood that some of the formaldehyde linkages may not be solely of the —CH$_2$ type but can also involve some extended units, such as CH$_2$OCH$_2$ and CH$_2$(OCH$_2$)$_n$OCH$_2$, or other possibilities (cf. Walker, supra). However, despite these uncertainties, NMR data on the carboxylated formaldehyde polymers of this invention indicate that the formaldehyde linkages consists essentially of the methylene linkage depicted in structure (A).

The formaldehyde polymers are prepared by heating approximately equimolar quantities of formaldehyde and the selected naphthalene compounds in an inert solvent, in the presence of an acid catalyst such as sulfuric acid, p-toluenesulfonic acid, methanesulfonic acid, or perchloric acid, for several hours. Depending on the nature of the formaldehyde polymer, the latter precipitates from the reaction mixture either directly on cooling to room temperature or upon quenching in water. The preferred solvent for the reaction is acetic acid, a solvent known to favor formation of polymers having oxygen-free linkages (Walker, supra, p. 439), such as those of the present invention.

The alkali metal salts of the carboxylated polymers of this invention are conveniently prepared by neutralization of a water or alcohol solution of the polymeric carboxylic acid derivative with alkali metal hydroxide solutions to the potentiometric endpoint. The salts are recovered by filtration, solvent stripping, or freeze drying, depending on the type of solvent used and whether the salt precipitates directly from the solvent media. Alternatively, carboxylic acid salts can be prepared by addition of at least stoichiometric quantities of an alkali metal oxide, carbonate, acetate, chloride, nitrate, or sulfate to the carboxylic acid polymer. The salts either precipitate directly and are collected, or they are isolated after solvent stripping. Purification of the carboxylate salt by dialysis is the preferred procedure for the more highly water soluble salts.

For testing the carboxylated naphthalene formaldehyde polymers of this invention, the in vitro test procedure we have employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

The alkali metal salts of the formaldehyde polymers of naphthoic and naphthylacetic acids of this invention are highly effective in reducing the deposition of plaque when tested by this in vitro test procedure. For example, the sodium salts of the formaldehyde polymers of 1-naphthoic acid and 1-naphthylacetic acid showed plaque reductions of 33% and 57%, respectively.

The formaldehyde polymers of this invention have a molecular weight of about 500 to about 10,000, preferably about 2,000 to 5,000. They are substantially soluble in water or mixed solvents comprising water and an organic solvent miscible therewith (generally at least 1% w/w).

EXAMPLE 1

Sodium Salt of 1-Naphthoic Acid/Formaldehyde Polymer

A solution of 17.2 g (0.100 mole) 1-naphthoic acid and 8.1 g (0.100 mole) 37% formaldehyde in 85 ml. glacial acetic acid was stirred and maintained at a temperature of 90°–110° C. during addition of 5.6 ml. (0.100 mole) 96% sulfuric acid over 10 minutes. The solution was maintained at 110° C. for another 24 hours, during which time the solution became progressively darker in color and some solids appeared. On cooling to 50° C., heavy precipitation of white solids occurred. Addition of 150 ml. water produced a heavier deposition of solids which was filtered, washed with water, and dried. The solids were slurried in boiling toluene, filtered hot, and dried to afford 11.1 g of the 1-naphthoic acid/formaldehyde polymer showing a softening point of about 220° C.

A solution of 1.8068 g of the 1-naphthoic acid polymer in 40 ml. methanol was neutralized from pH 2.5 to pH 8.0 with 16.6 ml. 0.512 N. methanolic sodium hydroxide. The neutralization equivalent value was 212.6. Removal of the solvent from the neutralized solution gave 1.9 g of the sodium salt of the polymer which was soluble in water and methanol.

EXAMPLE 2

Sodium Salt of 1-Naphthylacetic Acid/Formaldehyde Polymer

Into a flask was charged 18.6 g (0.100 mole) 1-naphthylacetic acid, 93 ml. glacial acetic acid, and 8.1 g (0.100 mole) 37% formaldehyde. With stirring, 5.6 ml. (0.100 mole) 96% sulfuric acid was added and the mixture heated at a gentle reflux (110° C.) for about 21 hours. On cooling to room temperature and dilution with 200 ml. water, heavy deposition of solids took place. The polymeric solids were filtered, washed with water, re-slurried in 200 ml. boiling water, and filtered hot. The moist solids were dried in vacuo at 60° C. to give 17.3 g of the 1-naphthylacetic acid/formaldehyde polymer, a tan colored powder.

A solution of 2.0251 g of the polymer was prepared in a mixture of 40 ml. acetone and 40 ml. tetrahydrofuran and neutralized to pH 7.7 with 20.6 ml 0.512 N methanolic sodium hydroxide solution. The sodium salt of the polymer precipitated and was filtered, washed with acetone, and dried. The neutralization equivalent value was 192 and in good agreement with the theoretical value of 198 for a 1:1 naphthylacetic acid/formaldehyde condensation polymer.

EXAMPLE 3

Sodium Salt of 2-Naphthoic Acid/Formaldehyde Polymer

Using the same procedure as described in Example 1, 2-naphthoic acid and 37% formaldehyde are reacted to afford the 2-naphthoic acid/formaldehyde polymer, which is then neutralized with sodium hydroxide to give the water soluble, polymeric sodium salt.

EXAMPLE 4

Potassium Salt of 2-Naphthylacetic Acid/Formaldehyde Polymer

In a manner similar to that described in Example 2, 2-naphthylacetic acid is converted to the corresponding formaldehyde polymer of structure (A), which, after neutralization with methanolic potassium hydroxide, affords the potassium salt.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidione; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A—Mouthwash Solution

| | |
|---|---|
| Barrier Agent | 0.5–2.0 % w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B—Mouthwash Solution

| | |
|---|---|
| Plaque Barrier Agent | 0.5–3.0 % w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C—Abrasive Dentifrice Gel

| | |
|---|---|
| Plaque Barrier Agent | 2.0–10.0 % w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D—Chewing Gum

| | |
|---|---|
| Plaque Barrier Agent | 1.0–11.0 % w/w |
| Gum Base | 21.3 |
| Sugar | 48.5–58.5 |
| Corn Syrup (Baume 45) | 18.2 |
| Flavors | 1.0 |
| | 100.0 |

EXAMPLE E—Nonabrasive Gel Dentifrice

| | |
|---|---|
| Plaque Barrier Agent | 0.05–30.0 % w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w | |
|---|---|---|
| Distilled Water | q.s. | |
| Sodium Saccharin (sweetener) | 0.20 | |
| Sodium Benzoate (preservative) | 0.30 | |
| FD & C Blue #1 (0.1% aq. soln.) | 0.27 | |
| D & C Yellow #10 (0.5% aq. soln.) | 0.50 | |
| Gelling agent | 18.00 | |
| Glycerol (Humectant) | 20.00 | |
| Cab-O-Sil M5 (Silicon Dioxide) | 1.00 | |
| Plaque Barrier Agent | 5.00 | (dry basis) |
| Flavor | 0.80 | |
| | 100.0 | |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. An oral hygiene composition comprising an effective amount for preventing deposition of dental plaque on teeth of a condensation polymer of formaldehyde with a naphthalene compound selected from the group consisting of 1-napthoic acid, 2-naphthoic acid, 1-naphthylacetic acid and 2-naphthylacetic acid, said polymer having repeating units of structure (A),

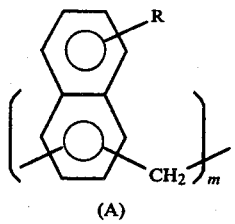

(A)

wherein R is selected from the group consisting of —COOM and —CH$_2$COOM, n is such that the molecular weight of said polymer is from about 500 to about 10,000, and M is selected from the group consisting of lithium, sodium, and potassium, in a pharmaceutically acceptable oral hygiene vehicle compatible with said polymer.

2. A method of preventing deposition of dental plaque on teeth comprising periodically applying to the teeth a composition of claim 1.

3. The method of claim 2 wherein said composition is applied from about 1 to about 3 times per day.

4. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *